United States Patent [19]

Hixson, Jr. et al.

[11] 4,264,514

[45] Apr. 28, 1981

[54] METHOD AND REAGENTS FOR MEASURING THE LEVEL OF CONJUGATED BILE ACIDS

[75] Inventors: Harry F. Hixson, Jr., Libertyville; Billy J. Green, Vernon Hills; Laurence M. Cummins, Libertyville; John W. Cole, Deerfield, all of Ill.

[73] Assignee: Abbott Laboratories, North Chicago, Ill.

[21] Appl. No.: 124,387

[22] Filed: Feb. 25, 1980

Related U.S. Application Data

[63] Continuation of Ser. No. 851,095, Nov. 14, 1977, Pat. No. 4,220,598, which is a continuation-in-part of Ser. No. 677,586, Apr. 16, 1976, abandoned.

[51] Int. Cl.$^3$ .............................................. C07J 9/00
[52] U.S. Cl. ...................................... 260/397.1; 424/1
[58] Field of Search .......................... 260/397.1; 424/1

[56] References Cited

U.S. PATENT DOCUMENTS

| | | | |
|---|---|---|---|
| 3,855,208 | 12/1974 | Rutner et al. | 260/239.57 |
| 3,935,245 | 1/1976 | Engelfried et al. | 260/397.1 |
| 4,069,305 | 1/1978 | Polito et al. | 260/239.5 |
| 4,207,308 | 6/1980 | Spenney | 260/397.1 |
| 4,220,598 | 9/1980 | Hixson, Jr. et al. | 260/397.1 |

OTHER PUBLICATIONS

New England Journal of Med. (1974) vol. 290, p. 1399.

*Primary Examiner*—Elbert L. Roberts
*Attorney, Agent, or Firm*—Neal O. Willmann

[57] ABSTRACT

A method and novel reagents useful for measuring the level of specific immunoreactive conjugated bile acids in a sample using labeled conjugated bile acid derivatives are disclosed.

12 Claims, No Drawings

METHOD AND REAGENTS FOR MEASURING THE LEVEL OF CONJUGATED BILE ACIDS

CROSS REFERENCE TO RELATED APPLICATION

This is a continuation of application Ser. No. 851,095 filed Nov. 14, 1977 now U.S. Pat. No. 4,220,598, which in turn is a continuation-in-part of U.S. Ser. No. 677,586, filed Apr. 16, 1976, now abandoned.

BACKGROUND OF THE INVENTION

It has been known generally that total bile acid concentration is elevated in patients with hepatobiliary diseases. The primary bile acids, cholic and chenodeoxycholic, are secreted by the liver as the glycine or taurine conjugates and stored in the gall bladder. Although some are absorbed from the gall bladder into the blood, most are secreted with the bile through the common bile duct into the lumen of the duodenum where they serve to facilitate the absorption of cholesterol and the digestion and absorption of fatty acids. The unused conjugated bile acids are absorbed into the blood vessels perfusing the duodenum and returned to the liver through the hepatic-portal system. Those bile acids not recovered in the duodenum are frequently converted to secondary bile acids by the action of intestinal flora. These too are absorbed into the blood and returned to the liver via the hepatic-portal system. In normal individuals the conjugated bile acids are removed from the circulation by the liver and recycled as conjugated primary bile acids. When the hepatocytes have been damaged by infection or chemicals, they are unable to recycle the bile acids in the usual manner. The quantity of affected cells is reflected by the quantitative relationship between the several primary bile acid conjugates and their corresponding secondary conjugates.

Numerous methodologies have been applied to the measurement of bile acids with varying degrees of success. Gas-liquid chromatography (G-LC) has been one of the most successful but suffers the disadvantages of requiring relatively large samples of patient serum, expensive equipment, and considerable sample pretreatment to isolate the conjugated from the unconjugated bile acids. Sample pretreatment includes isolation, saponification and derivation, rendering G-LC methods beyond the scope of ordinary laboratories.

A sensitive radioimmunoassay (RIA) for conjugates of cholic acid, a primary bile acid, was first described by Simmonds, et al., *Radioimmunoassay of Conjugated Cholyl Bile Acids in Serum;* Gastroenterology 65: 705–711 (1973). This Mayo Clinic group found their RIA to be specific for conjugates of cholic acid. Further clinical studies at the Mayo Clinic of Rochester, Minn., as reported by Korman, et al., in the *New England Journal of Medicine*, 290:1399 (1974), revealed elevated cholate conjugates in the sera of patients with chronic hepatitis in whom other liver function tests were normal and in patients with anticteric viral hepatitis. The clinical utility of this test was further demonstrated in 38 patients with chronic active hepatitis in whom the RIA of cholate conjugates proved to be a more sensitive indicator of disease than the traditional tests (bromosulfophthalein retention, prothrombin time, serum bilirubin, total proteins, alkaline phosphatase, and transaminase). Serum levels of bile acids, seen as the cholate conjugates, preceded serum enzyme elevations in those patients who ultimately relapsed. Although this method of the Mayo Clinic group showed good specifically for cholate conjugates, it could not distinguish between the glycine and the taurine cholate conjugates. G. M. Murphy, et al., *The Preparation and Properties of an Antiserum for the Radioimmunoassay of Serum Conjugated Cholic Acid,* Clinica Chimica Acta. 54: 81–89, (1974), repeated the work of Simmonds, et al., using a different method of hapten coupling and found essentially the same results.

While bile acids such as sulfolithocholic, cholic, chenodeoxycholic, deoxycholic, lithocholic and their conjugates with amino acids such as glycine and taurine can be prepared as the tritiated ($^3$H) forms, such as employed in the assays described above, these are undesirable as tracers in commercial immunoassays since they require: (1) the use of expensive beta counters, which most clinical laboratories do not have; (2) the use of scintillation fluids; (3) the use of special counting vials to which the tracer solution must be transferred; and (4) disposal of radioactive organic solvent waste.

Therefore, there is a need for a test that can be run directly on a serum sample yielding hepatic information about a specific bile acid conjugate and which can be used directly in an analytical instrument without special solution or vials.

SUMMARY OF THE INVENTION

Briefly, this invention relates to an assay for determining the level of specific conjugated bile acids in a sample. The assay comprises the steps of: providing an antiserum specific to one of the conjugated bile acids; mixing a serum sample with the antiserum and a novel reagent containing the same conjugated bile acid derivative which is tagged or labeled by known means with a labeling agent. Said labeling agents include physically detectable substances such as fluorescent chemicals, radioactive isotopes, electron spin resonating chemicals, and the like; incubating the sample mixture so as to bind the antibodies of the antiserum to the conjugated bile acid of the sample and to the labeled conjugated bile acid derivative, separating the antibody bond materials from the unbound materials; and measuring the level of the labeled derivative in either of the separated fractions whereby the quantity of the specific bile acid conjugate in the sample can be determined by comparison with standards.

The labeled reagent may be described more particularly as a compound selected from the formulae:

      I.

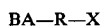      II.

wherein BA represents a bile acid selected from the group consisting of cholic, chenodeoxycholic, sulfolithocholic, deoxycholic and lithocholic; R is selected from the group consisting of

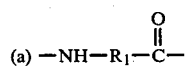

(b) —NH—R$_1$—NH—
(c) —NH—R$_1$—O— wherein R$_1$ is selected from the group consisting of lower alkyl C$_1$–C$_6$ and phenyl; and X is a moiety containing one of the aforementioned detectable tags or labeling agents.

DETAILED DESCRIPTION OF THE INVENTION

While the method described can be used to measure the level of conjugated bile acids in any sample, it will be described in particular with reference to the assay of serum.

A major function of the liver is the recycling of bile acids and acid conjugates. Impairment of this function results in altered patterns of bile acid conjugate concentrations in the serum. The quantitation of specific bile acid conjugates constitutes an assessment of hepatobiliary disease.

The present method provides a direct sensitive means of determining and measuring the level of a specific serum conjugated bile acid as an indication of liver function using conjugated bile acid derivatives. The present method is useful in determining whether a liver is diseased or damaged, and for determining the presence, in humans, of hepatobiliary diseases including viral hepatitis, hepatic malignancy, cholestasis, hepatic cirrhosis, and biliary atresia.

According to the present method it is essential to use a highly specific antiserum for each of the conjugated bile acids to be tested. The antisera which are specific to each of their respective bile acid conjugates have as a basis, a pure bile acid. The conjugated bile acids which may be obtained commercially may each be purified individually by thin-layer chromatography using conventional methods.

In the case of an isotope tag, it may be attached directly to the particular bile acid or conjugate thereof to be assayed. Preferably the radio label is incorporated into an amino acid such as tyrosine, tyramine, histidine and histamine. Polymers or copolymers containing these amino acids are also useful for labeling with the radioisotope.

The labeled amino acid or oligimer thereof may be appended directly to the bile acid or conjugate thereof. Preferably, however, the labeled moiety is attached to the bile acid or conjugate thereof with the aid of a spacer or connecting group selected from the following:

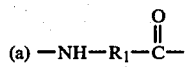

(b) —NH—R$_1$—NH—
(c) —NH—R$_1$—O— wherein R$_1$ is selected from the group consisting of lower alkyl C$_1$–C$_6$ and phenyl. This spacer is, in turn, connected to the bile acid or conjugate thereof.

For those bile acids and conjugate containing sulfate groups, the sulfate group may be replaced by a selenosulfate group containing $^{75}$Se as the radioisotope according to the method described by D. L. Klayman, Klayman and Gunther, editors, Organic Selenium Compounds: Their Chemistry and Biology, Interscience, New York, 1973, p. 151. Other reactions useful for the introduction of $^{75}$Se into the bile acid tracer may be found in Chapters III, IV, and others of that work. Cholylglycyltyrosine was prepared as hereinafter described and labeled with Iodine -125 by a modification of the chloramine T method of Greenwood, et al, (Greenwood, F. C., Hunter, W. M., and Glover), J. S., Biochem. J., 89, 114 (1963). The iodination occurs on the tyrosine ring and the compound cholyglycyliodotyrosine was found to be immunologically indistinguishable from cholyglycine using rabbit antisera prepared to a bovine serum albumin conjugate of cholylglycine.

The following examples will serve to elaborate the preparation of various bile acid conjugates which can be labeled and employed as gamma emitting tracers according to the teaching of this disclosure.

EXAMPLE 1

3-Sulfolithocholylglycylhistamine

A stirred solution at 20° C. is prepared from 100 mg. (0.2 mmole) of the pyridine salt of 3-sulfolithocholic acid, 3 ml. of pyridine, 40 mg. (0.25 mmole) of glycylhistamine and 0.3 ml. of water. To this is added a solution of 60 mg. (0.28 mmole) of dicyclohexylcarbodiimide dissolved in 1 ml. of pyridine. The clear reaction mixture is left under N$_2$ at about 15° C. for 24 hours, during which some crystals of dicyclohexylurea separate. One ml. of water is added, and after 2 hours the mixture is filtered. The clear filtrate containing the desired product is evaporated in vacuo without heat to give a solid residue. This is washed twice with 1.5 ml. of water and twice with 2 ml. of CH$_2$Cl$_2$, and dried in vacuo to a buff color powder of 3-sulfolithocholylglycylhistamine. The composition is confirmed by nmr spectrum.

EXAMPLE 2

Cholyltyrosine

With stirring at room temperature a solution is prepared from 1.45 g. (8 mmoles) of L-tyrosine, 1.69 g. (16 mmoles) of sodium carbonate and 30 ml. of water. Some material remains undissolved. During about 25 minutes, a solution of 2.0 g. of triformylcholic acid chloride in 30 ml. of dioxane is added. Much of the precipitate which forms redissolves during 2 hours stirring. The mixture is filtered and the filtrate is made alkaline by addition of 2 gms. of NaOH in 6 ml. of water. After standing 16 hours (to hydrolyze formate groups), the reaction mixture is evaporated in partial vacuum at 30° C. to remove some of the dioxane, and then cooled and acidified with 2NHC1 (foaming occurs) to precipitate the product at about pH3. The gummy precipitate is purified by washing (triturating) with dilute HCl, water and ether successively. The amorphous product is relatively insoluble in pure water, while it dissolves readily in ethanol or ethanol plus water. The nmr spectrum supports the structure as cholyltryosine.

EXAMPLE 3

3-Sulfolithocholylglycyl-ε-aminocaproyl-tyramine

The intermediate ε-aminocaproyl-tyramine hydrochloride is first prepared as follows: A cold stirred mixture of benzyloxycarbonyl-ε-aminocaproic acid (2.65 g), N-hydroxysuccinimide (1.15 g), 25 ml of dry dioxane, and 2.1 g of dicyclohexylcarbodi-imide is allowed to react at 3° C. for 24 hours. It is filtered (to remove by-product crystals) and the filtrate is evaporated in vacuo to a syrupy residue. Tyramine (1.31 g) and pyridine (8 ml) is added to the cold residue and stirred at 3° C. for 2 hours. The solution is held for 24 hours at room temperature and then evaporated in vacuo to a residue. The residue is diluted with water and acid (11 ml of 2N HCl) to give a crystalline precipitate of the product. This is washed with cold water. (A recrystallized sample melts at 107°–108° ). This benzyloxycarbonyl-ε- aminocaproyl-tyramine is then dissolved in ethanol containing one equivalent of aqueous 1 N HCl, and the solution is shaken under $H_2$ with palladium (10% on charcoal) for one hour. The filtrate, after removing the catalyst, is evaporated in partial vacuum to obtain a residue of the crystalline ε-aminocaproyl-tyramine hydrochloride.

A mixture of 1.0 millimole of the above hydrochloride, 1.0 millimole (0.55 g) of 3-sulfolithocholylglycine, 15 ml of pyridine, 3 ml of water, 0.122 g of $NaHCO_3$ and 0.210 g of dicyclohexylcarbodi-imide is stirred at 15° C. for 40 hours, and then filtered to remove by-product crystals of DCU. The filtrate is evaporated in vacuo, and water plus 3 ml of 1 N HCl is added to the residue to precipitate the amorphous product. The washed product is redissolved in 95% ethanol containing the theoretical amount of sodium carbonate (approx. 54 mg) and the filtered solution is evaporated to give the sodium salt of 3-sulfolithocholylglycyl-ε-aminocaproyl-tyramine.

EXAMPLE 4

Cholylglycyl Tyrosine

When the above procedure (cholyltyrosine) is repeated using a stirred solution of 0.73 g of L-tyrosine, 12 ml of water, 10 ml of 1N NaOH solution and 12 ml of dioxane, to which is added a solution of 1.1 g of triformylcholylglycine acid chloride dissolved in 12 ml of dioxane, the product is about 0.53 gs. of amorphous solid cholyglycyltyrosine. This product is soluble in ethanol or methanol, and gives an nmr spectrum showing the expected peaks for cholylglycyltyrosine.

The intermediate, triformylcholylglycine acid chloride is prepared using methods described in J. Am. Chem. Soc., 57, 393 (1935).

A representative fluorescent-labeled bile acid can be prepared by reacting cholylglycine with ethylene diamine using a water-soluble carbodiimide to give cholylglycinamidoethyl-amine which is then reacated with fluorescein isocyanate to give

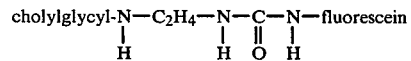

Assays utilizing fluorescent labels are well documented in the literature. The following references are particularly relevant to the present invention: Dandliker, W. B., et al., Immunochemistry, 1973, Vol. 10, pp 219–227, Pergamon Press; Smith, D. S. FEBS Leters, Vol. 77, No. 1, pp 25–27; Chen, R. F. Archives of Biochem and Biophysics 179, pp 672–681 (1977). Spin-labeled bile acids are used with electronspin resonance equipment and are similar to the fluorescent tagged bile acids except that the fluorescein isocyanate group is replaced by an amine group in which there is a functional group containing an unpaired electron, preferably a nitroxide group.

EXAMPLE 5

Spin Label

The procedure described in Example 3 is repeated using a stirred solution of 0.65 g of 4-amino-2,2,6,6-tetramethylpiperidino-1-oxy free radical instead of L-tyrosine. The product is cholylglycyl-4-amido-2,2,6,6-tetramethylpiperidinol-oxy, free radical. The product is soluble in ethanol and methanol.

Immunoassays employing spin labeled haptens have been developed for the detection of a number of compounds demonstrating biological activity. U.S. Pat. No. 3,996,764 specifically discloses morphine and codeine assay procedures that are based on electron-spin resonance detection.

We claim:

1. Sulfolithocholylglycylhistamine.
2. A compound according to claim 1 wherein the histamine is radiolabeled.
3. Cholyltyrosine.
4. A compound according to claim 3 wherein the tyrosine is radiolabeled.
5. A compound according to claim 3 wherein the tyrosine is radioiodenated.
6. A compound according to claim 5 wherein the radioiodine is $^{131}I$.
7. A compound according to claim 5 wherein the radioiodine is $^{125}I$.
8. Cholylglycyltyrosine.
9. A compound according to claim 8 wherein the tyrosine is radiolabeled.
10. A compound according to claim 8 wherein the tyrosine is radioiodenated.
11. A compound according to claim 8 wherein the radioiodine is $^{125}I$.
12. A compound according to claim 8 wherein the radioiodine is $^{131}I$.

* * * * *